(12) United States Patent
Shelnutt et al.

(10) Patent No.: US 7,704,489 B1
(45) Date of Patent: Apr. 27, 2010

(54) METHOD OF PHOTOCATALYTIC NANOTAGGING

(75) Inventors: John A. Shelnutt, Tijeras, NM (US);
Craig J. Medforth, Winters, CA (US);
Yujiang Song, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 658 days.

(21) Appl. No.: 11/542,506

(22) Filed: Oct. 3, 2006

(51) Int. Cl.
*B22F 1/00* (2006.01)
*B22F 1/02* (2006.01)
*C22C 1/05* (2006.01)

(52) U.S. Cl. .................... 424/9.61; 75/252
(58) Field of Classification Search ........... 424/9.52, 424/9.61; 75/252
See application file for complete search history.

(56) References Cited

U.S. PATENT DOCUMENTS 4,375,972 A    3/1983   Forgione et al.
6,123,923 A *  9/2000   Unger et al. ............... 424/9.52

OTHER PUBLICATIONS

John A. Shelnutt et al, "LDRD Final Report on Imaging Self-Organization of Proteins in Membranes by Photocatalytic Nano-Tagging" SAND2005-6948, Nov. 2005.

* cited by examiner

*Primary Examiner*—George Wyszomierski
*Assistant Examiner*—Weiping Zhu
(74) *Attorney, Agent, or Firm*—Carol I Ashby

(57) ABSTRACT

A nanotagged chemical structure comprising a chemical structure with an associated photocatalyst and a tagging nanoparticle (a nanotag) grown in proximity to the photocatalyst, and a method for making the nanotagged chemical structure. The nanoparticle is grown in proximity to the photocatalyst by using a photocatalytic reduction reaction.

9 Claims, 9 Drawing Sheets

METHOD OF PHOTOCATALYTIC NANOTAGGING

The United States Government has rights in this invention pursuant to Department of Energy Contract No. DE-AC04-94AL85000 with Sandia Corporation.

This patent application is related to a U.S. non-provisional patent application Ser. No. 10/887,535, filed on Jul. 8, 2004, now U.S. Pat. No. 7,374,599 B1, May 20, 2008, entitled "Dendritic Metal Nanostructures," which is incorporated herein by reference.

BACKGROUND OF THE INVENTION

This invention relates to a method for labeling or tagging a biological compound or structure with a metal or semiconductor particle and the structures produced by such methods. Conventional techniques for producing nanoparticle tags for spatially locating proteins are not compatible with retaining normal structure or with in-situ use. Traditionally, quantum-dot conjugates bound using, for example, streptavidin are larger than most proteins and the tagging process may interfere with biochemical processes and seriously distort the biological structures that one wishes to study. These methods also require modification of the protein target, for example, biotinylation, to enable binding of the tagging particle; this can disrupt the normal behavior of the target even before attachment of the tag. Since quantum dots are typically 10 to 25 nm in effective diameter, the distortion and interference resulting from their excessive size will frequently preclude their use in applications where retaining the activity or structure of the protein is desired.

BRIEF DESCRIPTION OF THE DRAWINGS

The accompanying drawings, which are incorporated in and form part of the specification, illustrate some embodiments of the present invention and, together with the description, serve to explain the principles of the invention.

DETAILED DESCRIPTION OF THE INVENTION

Figure 1:
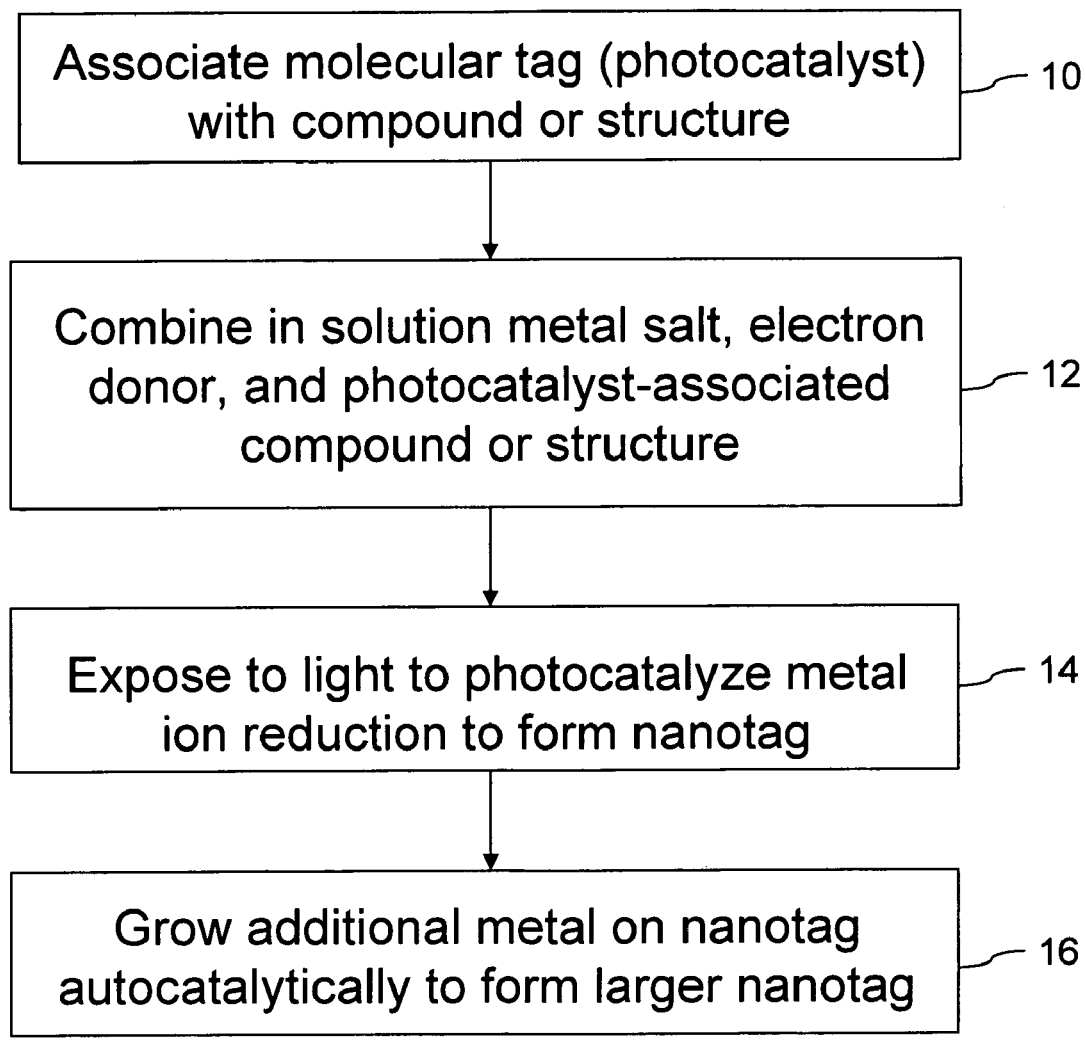
FIG. 1 illustrates a method for forming some embodiments of the invention.

This invention comprises a nanotagged chemical structure comprising a chemical structure with an associated photocatalyst and a tagging nanoparticle (a nanotag) grown in proximity to the photocatalyst, and it comprises a method for making the nanotagged chemical structure. The nanoparticle is grown in proximity to the photocatalyst by using a photocatalytic reduction reaction. In some embodiments, the photocatalyst is a porphyrin, where the term porphyrin is used broadly for the purpose of this invention to comprise porphyrins, chlorins, partially hydrogenated porphyrins and chlorins, and their metal-containing derivatives. The photocatalyst can be a non-porphyrin metal complex such as a metal polypyrrole complex, a metal polypyridine complex, or a metal phenanthroline complex if the electrochemical potential of the photoexcited complex or of the complex after reduction of the intial photoexcited complex is proper for the reduction of a desired metal ion. The chemical structure can be a support surface with which the photocatalyst can be associated through chemical bonding, hydrogen bonding, physical association, or some combination thereof. Examples of physical association include hydrophobic interactions, Van der Waal interactions, and electrostatic interactions.

The nanotagged chemical structures that are embodiments of this invention are very useful for labeling components of biological systems for detection and imaging purposes. Photocatalytic nanotagging with metal nanoparticles grown in vitro or in vivo in embodiments of this invention is especially well suited for imaging proteins and components of membranes and other structures to determine their structural organization and interactions. In embodiments of this invention, photocatalysts serve as molecular tags that can be associated with chemical structures or molecules. Photocatalytic tagging allows the use of a photocatalytically-formed nanotag that is located in close proximity to the photocatalyst; we define being in proximity to mean being less than approximately 10 nm from the location of the photocatalyst. The photocatalyst is termed a molecular tag; the nanotag is the nanoparticle whose growth is catalyzed by the molecular tag. Some embodiments employ a metal porphyrin complex as the molecular tag. For the purpose of this invention, the term porphyrin comprises porphyrins, chlorins, partially hydrogenated porphyrins and chlorins, and their metal-containing derivatives. The term metalloporphyrin also comprises metallochlorins. Other suitable photocatalysts include but are not restricted to anthracene, pyrene, and other polyaromatic hydrocarbons when using UV or visible light for photoexcitation of the photocatalyt. In some embodiments, a metalloporphyrin is selected to provide a suitable electrochemical potential under light excitation to catalyze the reduction of a metal ion to a neutral metal atom with the participation of an electron donor. The metal atoms combine to form a metal nanoparticle or nanocrystal that is a metal nanotag. While it is clear that this invention comprises as many metals as may have a reduction potential suitable for reduction using the photocatalysts described herein, some metals that provide suitable embodiments include but are not restricted to Ni, Pd, Pt, Cu, Ag, Au, Rh, Ir, and Ru.

The small size of a photocatalytically generated nanoparticle grown in proximity to the molecular tag interferes less with biomolecule structure, membrane binding, and other biochemical processes than do the >10-nm metal nanocrystals and semiconductor quantum dots used in conventional tagging methods. The small size of the molecular tag permits it to be carried by a protein during a biological process and, at a particular desired moment during the process, a metal nanotag can be photocatalytically grown in situ at the location of the molecular tag by exposure to light of a suitable wavelength. The small size of the molecular tag also permits its association with or within a chemical structure, such as a bilayer membrane, without significantly perturbing the general structure of the chemical structure. Using embodiments of this invention, biological processes such as the self-organization of proteins and other membrane components, for example, lipid rafts and caveolae, the transport of molecules through membranes, and the interactions of membrane surfaces with proteins and other species, such as, for example, drugs, can be visualized using nanotags.

Some examples of self-organization include protein association with intact lipid membranes, organization of proteins within and on membranes, and formation of membrane microdomains such as rafts and caveolae. Caveolae are relatively rigid and stable microdomains of a plasma membrane known to be rich in sphingolipids, cholesterol, and certain proteins. Some biological issues associated with membrane self-organization relate to the relative locations of various proteins and their association into large membrane-bound supercomplexes, the role of lipid rafts in this process, and the changes that occur in response to recognition and signaling events. Since rafts are generally small (approximately 25 nm in diameter), the use of small tags is desired to obtain substantially undistorted tagged structures. For rafts, determination of their size, number, and lipid/protein composition is of interest. Photocatalytic nanotagging of the lipids or raft proteins, such as caveolins-1, -2, -3, and glycosyl-phosphatidylinositol (GPI)-anchored proteins, can assist in characterizing the rafts and related structures. Caveolins play an anchoring role in membrane rafts and are suitable for photocatalytic nanotagging.

While the embodiments of this invention discussed in detail herein are presented with reference to biological structures and model structures, additional embodiments of this invention for nonbiological structures possessing similar chemical and structural properties as the proteins, lipids, and membranes described herein are also within the scope of this invention.

In some embodiments, metal nanoparticle tags are grown in the following way. A porphyrin-associated structure or compound is prepared wherein the porphyrin associated with the structure or compound is a metalloporphyrin or a metallochiorin that is capable of forming a radical upon absorption of light in the presence of an electron donor; the radical has a potential suitable for reducing a metal ion. The term porphyrin and its derivatives are employed for the purpose of this invention to include by definition porphyrin-related analogs wherein substituent moieties are added to the foundational heterocycle. Hence, these terms include their derivitized analogous forms, including those forms which have been partially hydrogenated, forms wherein a metal ion has been bound to the heterocycle, and forms where substituent groups, such as, for example, hydrophobic groups such as, for example, lipids, have been bound to the heterocycle.

In some embodiments, the following porphyrins and/or their salts may be used: tin(IV) 2,3,7,8,12,13,17,18-octaethylporphyrin (SnOEP), tin(IV) 5,10,15,20-tetra(4-sulfonatophenyl)porphyrin (SnTPPS4), tin(IV) protoporphyrin (IX) (SnProP), tin(IV) tetra(N-methyl-4-pyridyl)porphyrin (SnNMePyP), tin(IV) uroporphyrin (SnUroP), tin(IV) tetra (4-pyridyl)porphyrin (SnTPyP), tin(IV) tetraphenylporphyrin (SnTPP), tin(IV) tetra(4-carboxyphenyl)porphyrin (SnTCPP), tin(IV) tetrakis(N-octadecyl-r-pyridyl) porphyrin (SnP18), oxo-antimony(V) 2,3,7,8,12,13,17,18-octaethylporphyrin (SbOOEP), oxo-antimony(V) 5,10,15,20-tetra (4-sulfonatophenyl)porphyrin (SbOTPPS4), oxo-antimony (V) protoporphyrin(IX) (SbOProP), oxo-antimony(V) tetra (N-methyl-4-pyridyl)porphyrin (SbONMePyP), oxo-antimony(V) uroporphyrin (SbOUroP), oxo-antimony(V) tetra(4-pyridyl)porphyrin (SbOTPyP), oxo-antimony(V) tetraphenylporphyrin (SbOTPP), oxo-antimony(V) tetra(4-carboxyphenyl)porphyrin (SbOTCPP), oxo-antimony(V) tetrakis(N-octadecyl-r-pyridyl) porphyrin (SbOP18). The preceding abbreviations are understood to include the porphyrin and/or its salts and the chlorin analogs.

In some embodiments, the metalloporphyrin serves as the molecular tag. The molecular tag is associated with a chemical structure or molecule by one or more of several interactions, including but not restricted to covalent bonding, hydrogen bonding, van der Waals interactions, hydrophobic interactions, and electrostatic interactions. A buffered solution containing a metal salt and a weak electron-donor molecule is combined with the porphyrin-associated structure or compound. When exposed to light of an appropriate wavelength, the photoexcited metalloporphyrin is reduced by the electron donor, producing a porphyrin radical that is capable of reducing metal ions. The light employed is determined by the photoexcitation properties of the molecular tag (photocatalyst); in many embodiments, this will be visible light. Since the photoreaction is cyclic, each photocatalyst molecule can reduce many metal ions as additional photons are absorbed. The resulting metal nanoparticle forms in close proximity to the porphyrin. After photochemically initiating the reduction process, in some embodiments growth of the nanoparticle can proceed autocatalytically (not needing continuing photocatalysis) to an extent substantially determined by the solution concentration of the metal ion and the time duration of autocatalytic growth.

FIG. 1 illustrates a method for forming some embodiments of the invention. A molecular tag (photocatalyst) is associated with a chemical structure or compound 10. Association refers to a process of connecting, joining together, or combining. The nature of the association can be by chemical bonding, physical association, or some combination thereof. For example, in some embodiments, a hydrophobic photocatalyst such as a hydrophobic metalloporphyrin can be associated with a chemical structure by residing within lipid bilayer of a membrane or liposome. In other embodiments, a metalloporphyrin might be associated with a membrane or liposome by being covalently bonded to a lipid or other hydrophobic moiety that is incorporated into the membrane or liposome. In other embodiments, a metalloporphyrin might be associated with a protein by covalent bonding, hydrogen bonding, and/or electrostatic interactions.

The photocatalyst-associated compound or structure forms a photosensitizable structure that is combined in solution with a metal salt and an electron-donor species 12. The solution is exposed to light of a suitable wavelength to photoexcite the photosensitizable species, forming a photoexcited structure. Reaction of the photoexcited species with the electron-donor species forms a photocatalyst for the reduction of the metal ions to form metal atoms 14. Multiple repetitions of this photocatalyzed reduction form a metal nanoparticle as a nanotag in proximity to the photocatalyst.

In some embodiments, autocatalytic growth of the nanotag may be used to form larger nanotags from the initial smaller nanotags formed photocatalytically 16.

Figure 2:
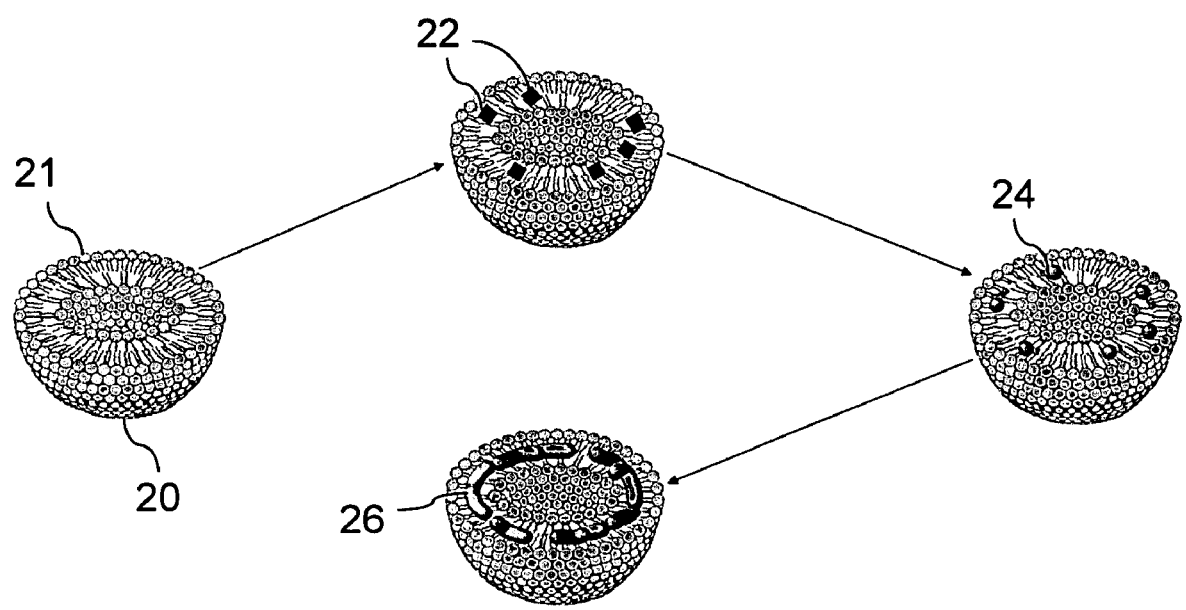
FIG. 2 illustrates an embodiment wherein metal nanoparticles are grown within a bilayer using a hydrophobic metalloporphyrin as the photocatalyst for metal reduction. Additional autocatalytic growth of metal on the photocatalytically formed nanoparticles is also shown.

FIG. 2 illustrates schematically an embodiment of the invention involving liposomes as the chemical structure and a porphyrin as the photocatalyst. A cut-away view of approximately half of a liposome 20 is shown. The liposome comprises a bilayer of lipid molecules 21. A hydrophobic porphyrin 22, is incorporated within the bilayer of the liposome. Photocatalytic growth of metal nanoparticles in proximity to the incorporated porphyrin produces particles 24 as nanotags within the membrane bilayer. If desired, further autocatalytic growth of metal on the photocatalytically formed nanoparticles can be employed to produce larger nanoparticles 26 as larger nanotags.

In different embodiments, the nanotags can comprise a metal with a suitable reduction potential to be reduced by the photocatalyst. For each embodiment, a suitable metal salt is used as the metal atom source. Some examples of such metals include but are not restricted to silver, platinum, lead, and gold. Examples of metal salts suitable for some embodiments include a gold(I) thiourea complex, a tetrachloroplatinate salt such as, for example, $K_2PtCl_4$, and silver nitrate ($AgNO_3$). For some embodiments, examples of suitable electron donors to use in the formation of the nanotagged structure include ascorbic acid, methanol, ethanol, ethylenediamine tetraacetic acid (EDTA) and its salts, nitrite ion, and tertiary amines, such as, for example, ethanolamine and triethylamine. Other electron donors that may be suitable include electron donors that are relatively weak electron donors with a redox potential in the range of 0.0 to +1.0 V versus the normal hydrogen electrode (NHE). Somewhat stronger electron donors may also be used provided they are kinetically slow in reducing the metal salt or metal complex directly so that reduction is predominantly due to reduction by a porphyrin species and not directly by the electron donor molecule. An example of this is provided by ascorbic acid, which has a redox potential of approximately −0.3 V at pH 3. When the photocatalyst is a porphyrin, the photoexcited porphyrin can react with the electron donor to form a porphyrin radical. The metal salt is selected based upon the desired composition of the nanoparticle and the reduction potential of the metal ion relative to the electrochemical potential of the porphyrin radical produced by photoexcitation. In some embodiments, it is desirable to select a metal salt that produces solutions that are substantially transparent at the wavelength employed to photoexcite the porphyrin. Examples of metal salts that have been used for growth of gold, platinum, and silver nanoparticles include a gold(I) thiourea complex, potassium tetrachloroplatinate ($K_2PtCl_4$), and silver nitrate ($AgNO_3$).

Figure 3:
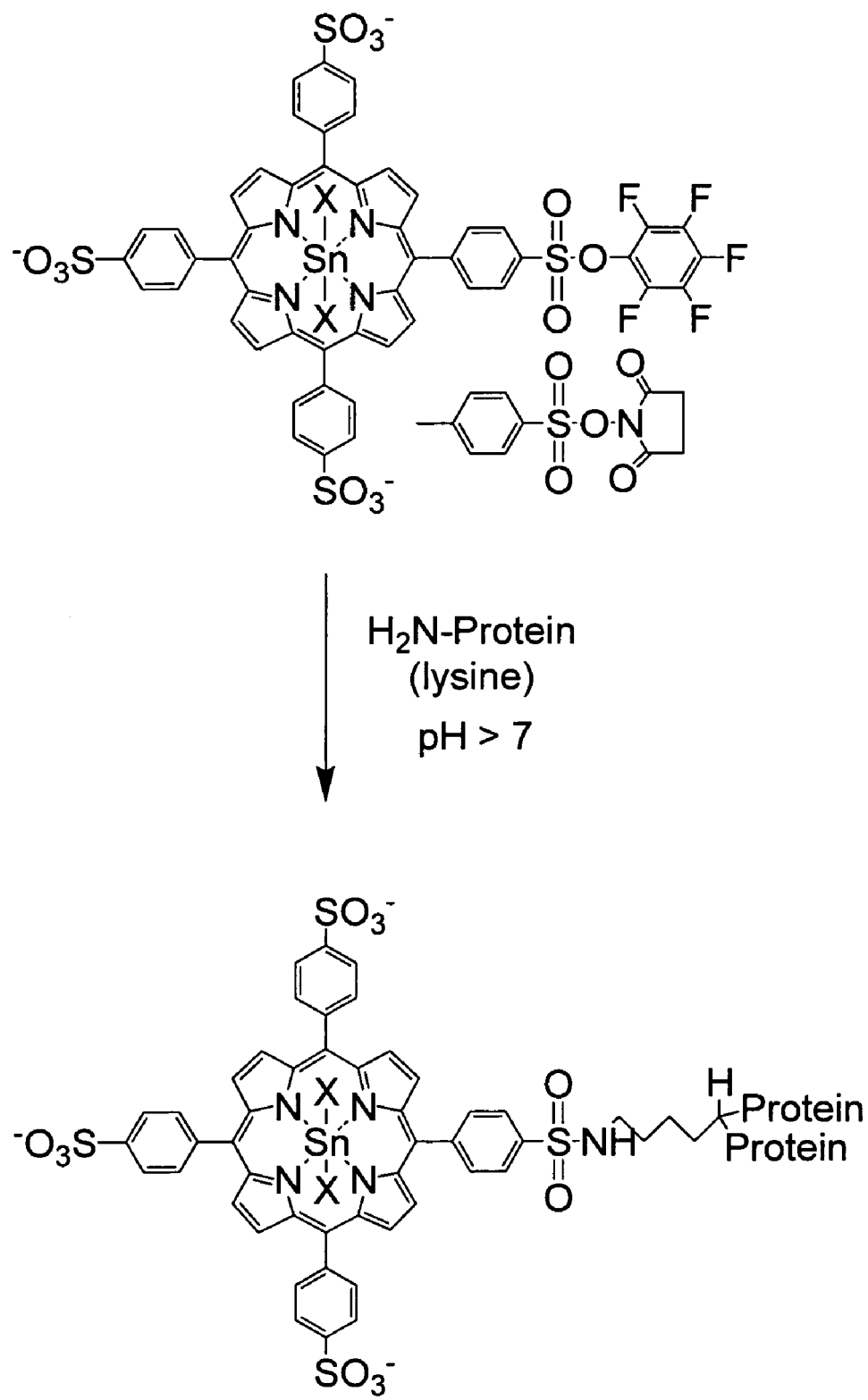
FIG. 3 illustrates porphyrin-lysine hybrids of proteins made by formation of sulfonamide linkages using activated sulfonyl esters (X=OH or $H_2O$).

There are numerous embodiments employing various porphyrin-associated structures or compounds. The structure or compound can contain a porphyrin group as part of its regular structure. An example of such a structure is hemoglobin, which contains four Fe(II) protoporphyrin moieties. The structure can contain a porphyrin group that has been covalently attached by reaction with an initial structure, such as, for example, a protein. FIG. 3 illustrates the synthesis of porphyrin-protein species by formation of sulfonamide linkages with lysine units of the protein using activated sulfonyl esters (X=OH or $H_2O$).

Figure 4:
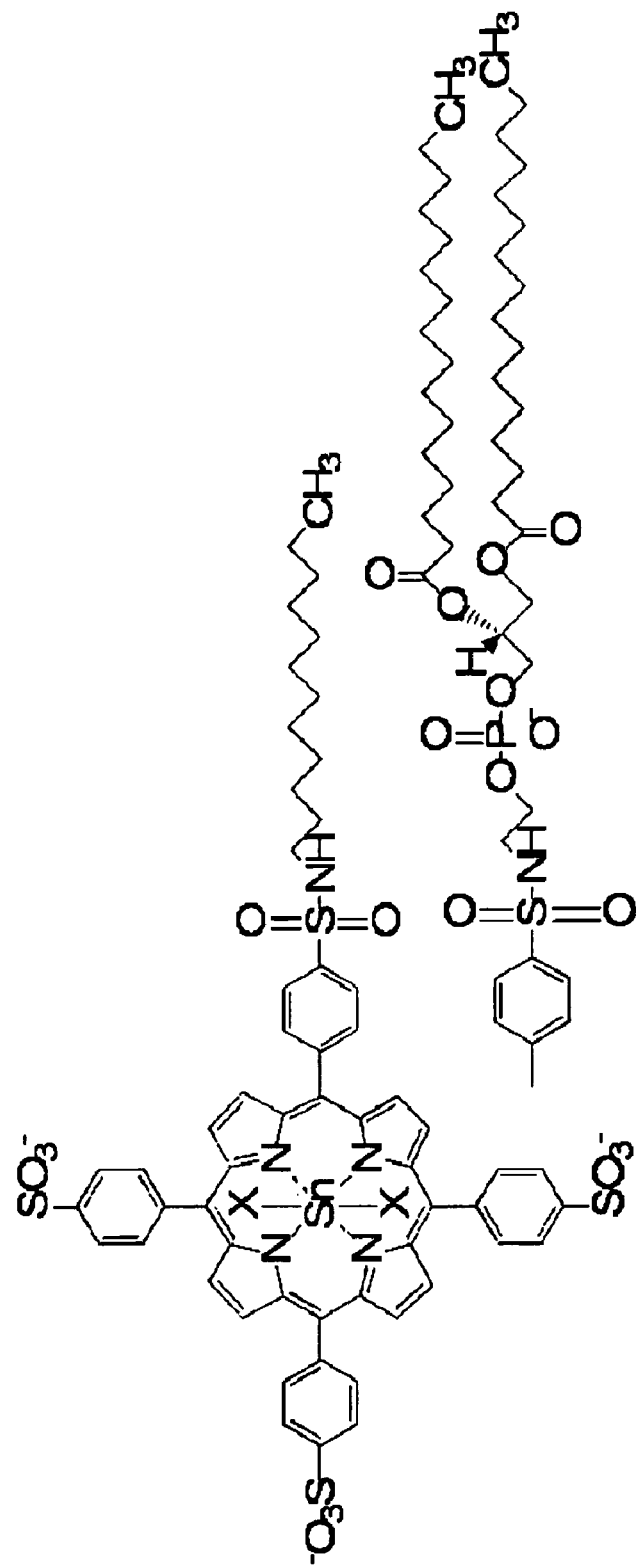
FIG. 4 illustrates two examples of conjugates that can be prepared by coupling a porphyrin sulfonyl chloride with an aminolipid. Illustrates compounds formed using dodecylamine and 1,2-dioctadecanoyl-sn-glycero-3-phosphoethanolamine.

In some embodiments, the structure can possess physical characteristics that favor the association of a photocatalyst with the structure. An example of such a structure is a liposome, which is an artificial microscopic vesicle consisting of an aqueous core enclosed in one or more phospholipid layers. A hydrophobic porphyrin or a polyaromatic hydrocarbon can be localized within the lipid layer. Another example of such a structure is the incorporation into a membrane of the hydrophobic portion of a porphyrin-lipid conjugate. One example of such a conjugate can be prepared by coupling a porphyrin sulfonyl chloride with an aminolipid; two such molecules are illustrated in FIG. 4.

In some embodiments, the nanotagging method is employed to study protein self-organization in membranes using proteins that do not need to be chemically modified because they naturally bind porphyrin molecules. For example, in some embodiments, a photocatalytic porphyrin is bound to the protein, membrane, or other structure or compound at a site where a natural porphyrin would normally bind. One example of such a natural porphyrin is a heme group, for example, protoporphyrin. In some embodiments, a tin porphyrin is bound in the heme binding sites. Examples of some porphyrins that may be used include but are not restricted to Sn(IV) protoporphyrin (SnProtoP) and oxo-antimony(V) protoporphyrin (SbOProP). In one embodiment, hemes were extracted from human hemoglobin as follows. A solution of the human hemoglobin was acidified with a solution of acetone and HCl, stirred to remove the heme groups, and centrifuged to recover the resulting apoprotein. The apoprotein was then re-suspended in acidified acetone and centrifuged again, with the pink supernatant fluid being discarded. This process was repeated several times to remove residual heme. The pellet of apoprotein was then dissolved in water and dialysed against phosphate buffer at pH 6.8 and then against Tris HCl buffer. The apoprotein was then centrifuged and filtered to remove precipitated protein. SnProtoP was added slowly to a cooled and gently stirred solution of the apoprotein to produce a solution with a SnProtoP concentration approximately 8 times the apoprotein concentration. This mixture was then incubated in the dark. The resulting Sn-hemoglobin was chromatographed on a gel filtration column to remove excess SnProtoP. The Sn-porphyrin-reconstituted hemoglobin showed a somewhat red-shifted UV-visible absorption spectrum compared to SnProtoP in the same buffer solution, confirming binding of SnProtoP to the protein. The Sn porphyrins contained in the Sn-reconstituted hemoglobin were photocatalytically active for reducing methylviologen. This indicates that they retain the ability to catalyze growth of a metal or semiconductor nanoparticle tag near the active sites of the protein.

Figure 5:
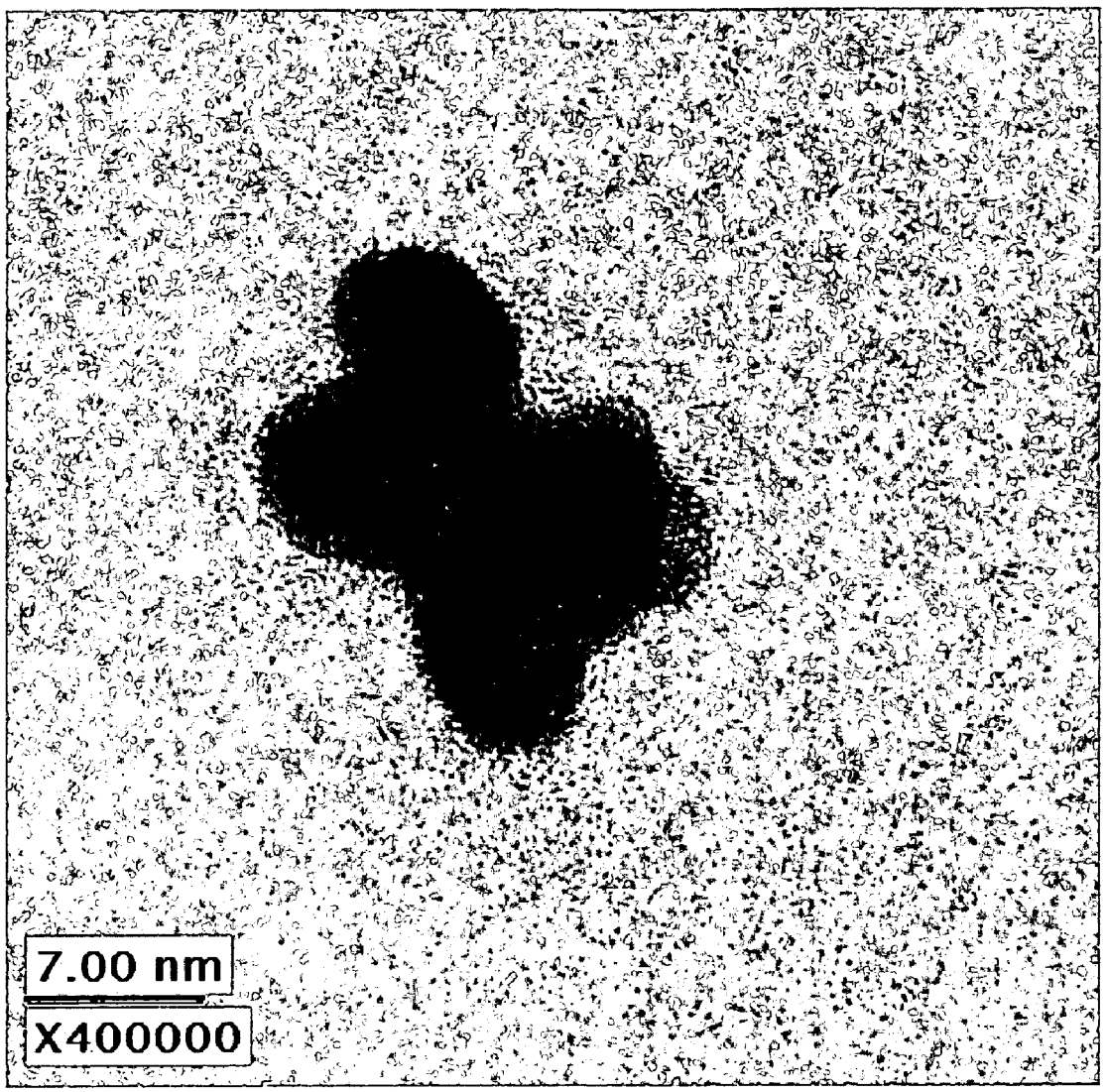
FIG. 5 is a transmission electron micrograph (TEM) illustrating a cluster of gold nanoparticles produced in the presence of Sn-reconstituted hemoglobin using Sn-substituted heme groups as photocatalysts for the reduction of gold(I) thiourea complex with ascorbic acid.

Gold nanoparticles were grown as nanotags on Sn-hemoglobin and are illustrated in the transmission electron micrograph (TEM) image shown in FIG. 5. The four heme units that comprise hemoglobin have generated corresponding gold nanoparticles. Gold(I) thiourea complex was used as a gold source; for this embodiment, is has the advantage of not substantially absorbing the visible light used to photoexcite the Sn-porphyrin. The gold(I) thiourea complex was added to buffered solution containing a weak electron-donor molecule (ascorbic acid in some embodiments). When exposed to visible light, the photoexcited porphyrin was reduced by the electron-donor molecule, producing a porphyrin radical capable of reducing the gold(I) ions from the solution. Gold is a desirable metal nanotag for some embodiments because is easy to image by TEM and also serves to optically label the protein. The nanotagged structure is consistent with the metal nanoparticles residing on the surface of the hemoglobin tetramers in close proximity to the bound porphyrin photocatalyst molecules.

In some embodiments, a photocatalyst is incorporated into a hydrophobic region of a structure, such as, for example, a lipid bilayer. Two examples of such embodiments involve a membrane or membrane model, such as a liposome. In some embodiments, hydrophobic porphyrins can be incorporated directly into the lipid bilayer. In other embodiments, the porphyrin can be covalently attached to a lipid head group or other hydrophobic head group. An example of another hydrophobic head group is the N-octadecyl-4-pyridyl group. In the first type of embodiments, the metal nanotags that are formed can be located within the bilayer. In the latter type of embodiments, the porphyrin is located at the surface of the bilayer, and the metal nanotag will reside on the surface of the membrane.

In an embodiment employing liposomes, Sn(IV) octaethylporphyrin (SnOEP) was incorporated into the interior of the lipid bilayer comprising the liposome. Stock solutions in chloroform of 5 mL of 1,2-dioctadecanoyl-sn-glycero-3-phosphocholine (DSPC) (1 mM), 5 mL of cholesterol (1 mM), and 0.2 mL of SnOEP (5 mM) were added to a round-bottomed flask. The flask was connected to a rotary evaporator and dried at 35° C. to form a thin lipid film on the inside wall of the flask. The residual traces of solvent were removed by overnight drying under high vacuum. The film was then hydrated in 10 mL of an aqueous solution of ascorbic acid (150 mM) for one hour at 65° C. to form multilamellar liposomes. The multilamellar liposomes were then sonicated briefly in a bath to reduce the average size of the vesicles and then extruded through a 200-nm pore polycarbonate membrane in a LIPEX™ liposome extruder (Northern Lipids Inc. Vancouver, Canada). The liposomes were extruded at least 10 times to ensure uniform size distribution and to filter out the undissolved SnOEP. The liposomes have an average size of 170-nm in diameter, which was measured on a Protein Solutions DynaPro LSR (Lakewood, N.J.) at 25° C. with a laser wavelength of 782.4 nm. For the measurement, at least 20 data acquisitions with a baseline error threshold below 1% were obtained and averaged to yield the particle size. In some embodiments, platinum (II) solutions were prepared by dissolving $K_2PtCl_4$ in water at room temperature and were sometimes aged at least 24 hours before use. Aging the platinum solution disproportionates the complex into an equilibrium mixture of 42% $Pt(H_2O)_2Cl_2$, 53% $Pt(H_2O)Cl_3^-$, and 5% $PtCl_4^{2-}$. In some embodiments, before irradiation, the Pt(I1) aqueous solution was mixed with liposomal suspension prepared in ascorbic acid solution. In some other embodiments, the liposomal suspension was prepared in water. In these embodiments Pt(II) solution and ascorbic acid are added to the liposomal suspension before irradiation.

Figure 6A:
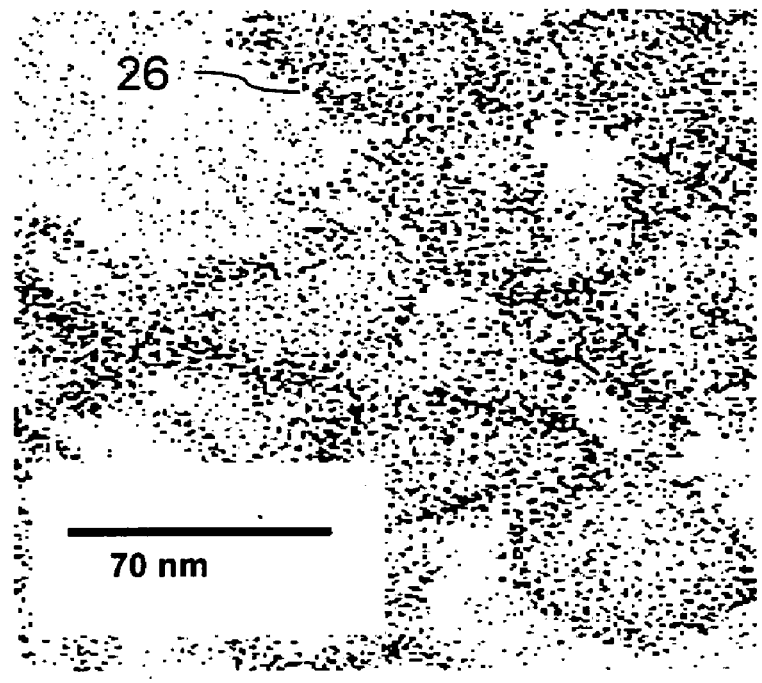
FIG. 6 is a TEM illustrating Pt nanoparticles formed within a liposomal bilayer. a) Pt nanoparticles formed by photocatalytic growth. b) Pt nanodendrites initiated photocatalytically and enlarged by autocatalytic growth.

FIG. 2 illustrates schematically the steps of an embodiment involving liposomes. A cut-away view of approximately half of a liposome 20 is shown. The liposome comprises a bilayer of lipid molecules 21. A hydrophobic porphyrin 22, SnOEP in some embodiments, is incorporated within the bilayer of the liposome. Photocatalytic growth of metal nanoparticles in proximity to the incorporated porphyrin produces particles 24 within the membrane bilayer. Pt nanoparticles grown on approximately 120-nm-diameter liposomes containing a high loading of SnOEP when exposed to intense white light are shown in the TEM image presented in FIG. 6a.

Figure 6B:
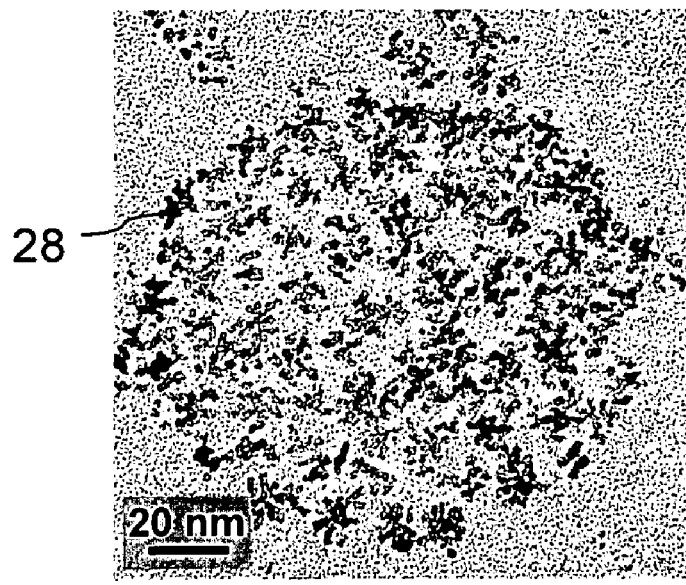
Figure 7:
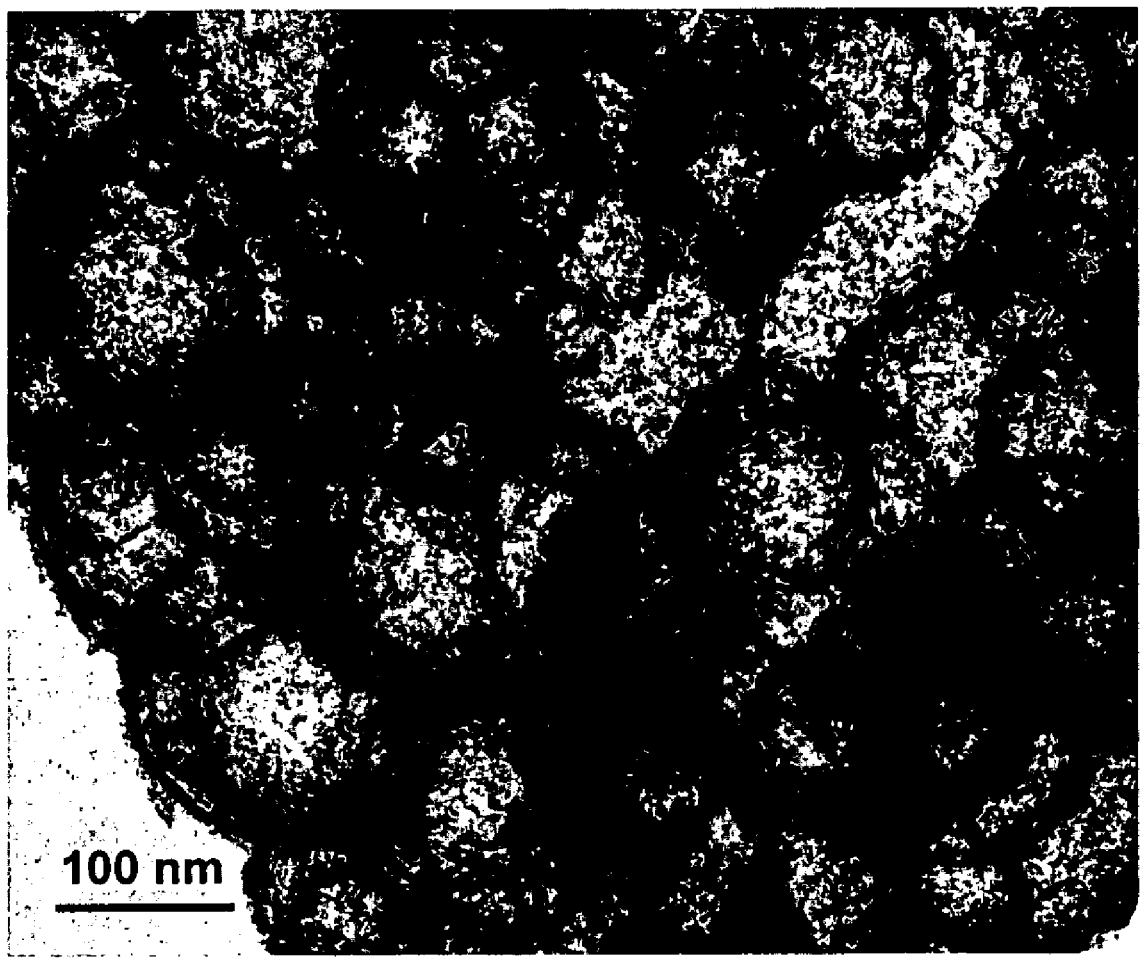
FIG. 7 is a TEM illustrating an embodiment where autocatalytic growth has produced a network of Pt dendrites that preserve the substantially spherical structures of liposomes upon drying.

Autocatalytic growth of Pt on the photocatalytically initiated Pt seed particles (small nanotags) can be used in some embodiments to grow approximately 2-dimensional dendritic nanostructures to a desired diameter by controlling the amount of platinum complex available for growth on the photocatalytically generated seed particles. FIG. 6b presents a TEM image of Pt nanodendrites 28 grown within the bilayer membrane of an approximately 140-nm-diameter liposome containing intramembrane SnOEP when exposed to intense white light for 30 minutes. Autocatalytic growth follows initial photocatalytic growth. A rigid network of Pt nanodendrites can be grown when the neighboring nanodendrites grow together. This structure preserves the essentially spherical structure of the liposome upon drying on a TEM grid. A collection of such structures is illustrated in FIG. 7.

In some embodiments, the porphyrin is associated with a lipid bilayer using a hydrophobic substituent appended to the porphyrin ring structure. Such porphyrin-lipid hybrids can be incorporated into the bilayer, leaving the porphyrin exposed at the hydrophilic surface of the lipid bilayer.

Figure 8:
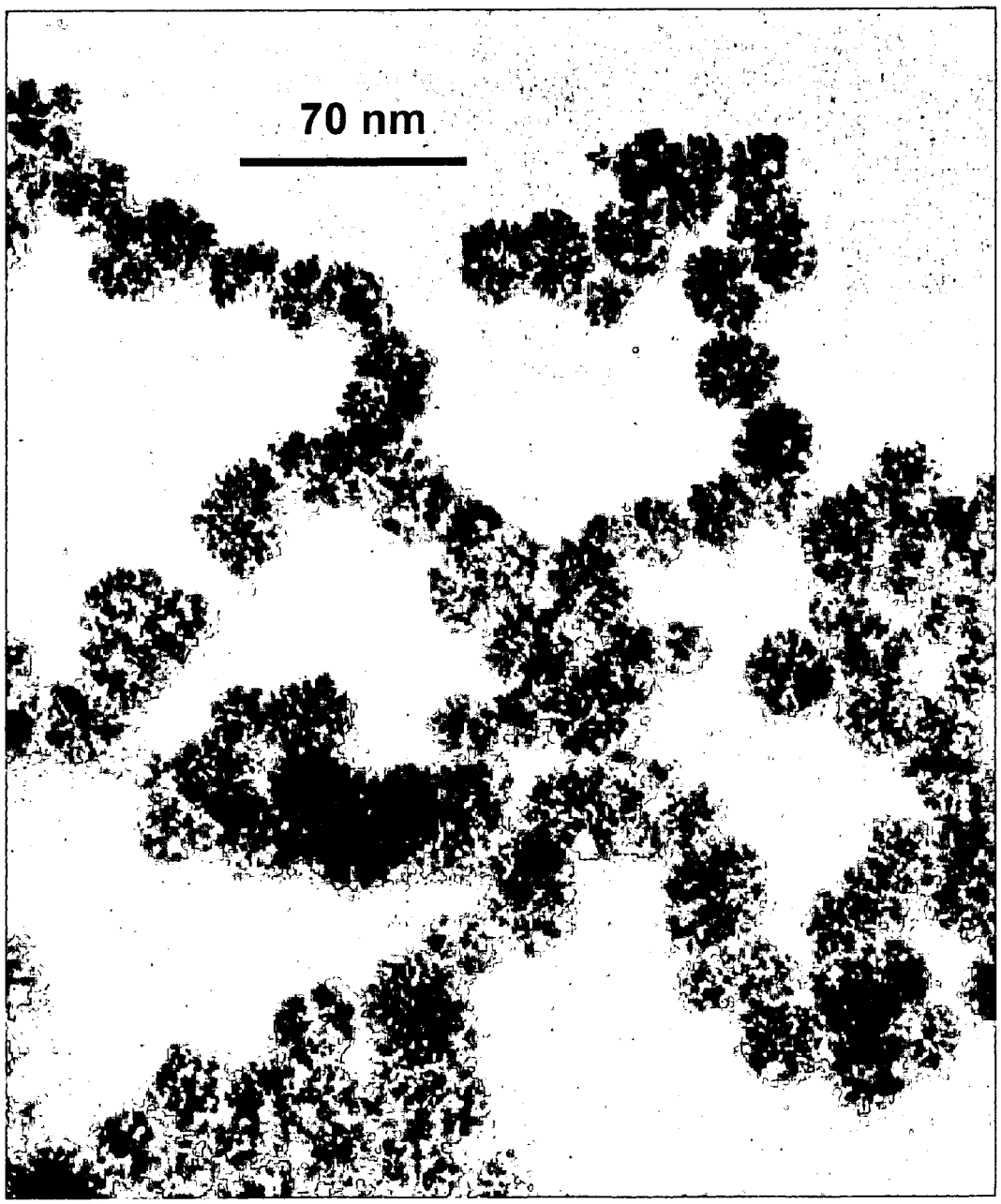
FIG. 8 is a TEM illustrating an embodiment where globular Pt dendrites were produced by illumination of nanostructures formed of SnTPPS-C12.

FIG. 8 shows globular dendrites of platinum that are obtained by shining white light from an incandescent source onto a solution of the dodecyl lipoporphyrin (SnTPPS-C12) in the absence of liposomes. FIG. 4 illustrates two examples of photocatalytic porphyrin-lipid conjugates that can be produced by coupling a porphyrin sulfonyl chloride with an aminolipid; this produces a hydrophobic "tail" substituent that can be incorporated into a lipid bilayer or other hydrophobic structure. The conjugates in FIG. 4 are abbreviated as SnTPPS-C12 and SnTPPS-DSPE. A wide range of other amines with hydrophobic tail substituents can also be used to form porphyrin compounds with hydrophobic "tails" suitable for incorporation into a hydrophobic environment as long as the amine will react with the sulfonyl substituent of the porphyrin. It is intended that embodiments of this invention should include such additional hydrophobic species. In other embodiments, for example, other lipids may be used as the hydrophobic tail substituent. The important physical characteristic of the tail is its ability to be incorporated into the bilayer. The dihydroxide complexes are shown in FIG. 4; water can also be a ligand at low pH. In the absence of a lipid bilayer, lipoporphyrins are capable of self-aggregating to form small micelles, as in the structures of FIG. 8.

Figure 9:
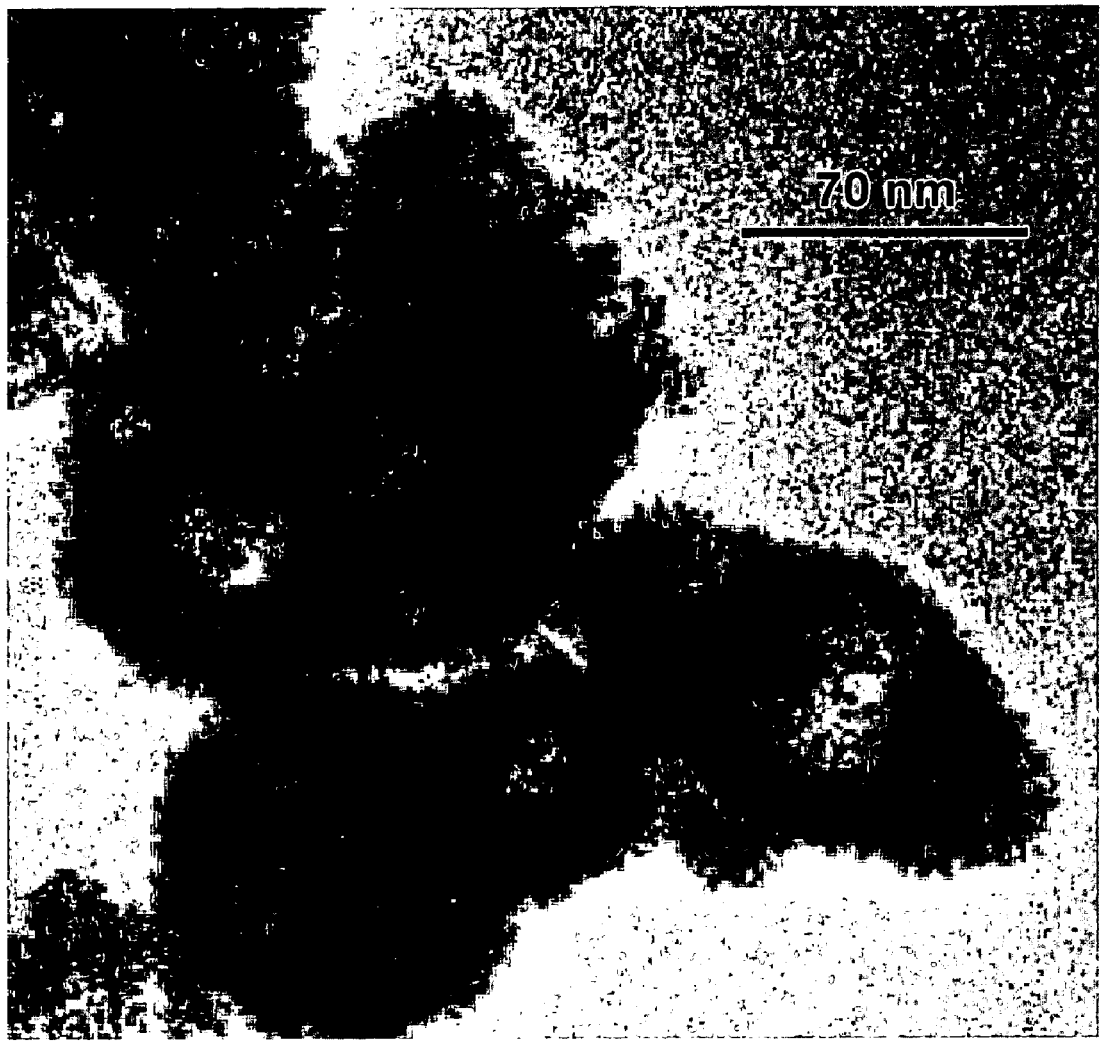
FIG. 9 is a TEM illustrating an embodiment where platinum dendritic structures coat DSPC/cholesterol liposomes containing SnTPPS-C12.

FIG. 9 shows embodiments displaying the platinum growth after addition of unilamellar DSPC/cholesterol liposomes to the solution of the Sn lipoporphyrin, SnTPPS-C12. We expect the three negative charges of the porphyrin head group of the lipids in FIG. 4 to repel other similarly labeled lipid molecules, leading to even dispersal of the porphyrin labels over the liposomal surface. Dendritic sheet growth occurs when the seeds initiating platinum growth are within a bilayers; porphyrin head groups anchored to the surface of a liposome grow globular dendrites on the liposomal surface. The furry-looking appearance of the platinum on the surface of the lipoproteins/liposome structures shows the formation of dendrites at the liposomal surface rather than within the bilayer.

In some embodiments, hybrids between a drug or a pathogen molecule and a photocatlytic metalloporphyrin can be made and bound to receptor sites. Metal nanotags can then be grown to form the nanotagged structure that is subsequently imaged. Imaging techniques suitable for some embodiments of the invention include but are not limited to fluorescence, electron microscopy (EM), and atomic force microscopy (AFM). Three types of EM include transmission electron microscopy (TEM), scanning TEM (STEM), and scanning electron microscopy (SEM).

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A nanotagged structure comprising:
   a chemical structure comprising an associated photocatalyst molecule; and
   a metal nanotag proximate to the associated photocatalyst molecule and located within an electron-transfer length of a radical form of the associated photocatalyst molecule.

2. The nanotagged structure of claim 1, wherein the chemical structure is a protein, a membrane, a biomolecule, a drug, or a liposome.

3. The nanotagged structure of claim 1, wherein the associated photocatalyst molecule comprises a porphyrin.

4. The nanotagged structure of claim 3, wherein the porphyrin comprises a metal selected from Sn, Sb, Ge, Zn, and Mg.

5. The nanotagged structure of claim 1, wherein the associated photocatalyst molecule is a metalloporphyrin, a metallochlorin, a metallophthalocyanine, a metallochlorophyll, a metal polypyrrole complex, a metal polypyridine complex, or a metal phenanthroline complex.

6. The nanotagged structure of claim 1, wherein the associated photocatalyst molecule is SnOEP, SnTPPS4, SnProP, SnNMePyP, SnUroP, SnTPyP, SnTPP, SnTCPP, SnP18, SbOOEP, SbOTPPS4, SbOProP, SbONMePyP, SbOUroP, SbOTPyP, SbOTPP, SbOTCPP, or SbOP18.

7. The nanotagged structure of claim 1, wherein the metal nanotag is a metal nanoparticle.

8. The nanotagged structure of claim 1, wherein the metal nanotag comprises at least one of Ni, Pd, Pt, Cu, Ag, Au, Rh, Ir, and Ru.

9. A nanotagged structure comprising:
   a chemical structure comprising an associated porphyrin photocatalyst molecule; and
   a metal nanotag proximate to the associated porphyrin photocatalyst molecule and located within an electron-transfer length of a radical form of the associated photocatalyst molecule.

* * * * *